United States Patent [19]

Shibayama et al.

[11] Patent Number: 4,663,443

[45] Date of Patent: May 5, 1987

[54] N-SUBSTITUTED NEURAMINIC ACID DERIVATIVES

[75] Inventors: Shohei Shibayama, Tokorozawa; Shoji Yoshimura, Iruma; Masayoshi Ito, Kunitachi; Yoshiyasu Shitori, Tokyo; Tomoya Ogawa, Musashino, all of Japan

[73] Assignee: Kanto Ishi Pharmaceutical Co., Ltd., Tokyo, Japan

[21] Appl. No.: 729,360

[22] Filed: May 1, 1985

[30] Foreign Application Priority Data

May 1, 1984 [JP] Japan .................................. 59-88193

[51] Int. Cl.$^4$ .............................................. C07H 5/06
[52] U.S. Cl. .................................... 536/4.1; 536/18.2; 536/53
[58] Field of Search ........................... 536/4.1, 18.2, 53

[56] References Cited

U.S. PATENT DOCUMENTS

| | | | | |
|---|---|---|---|---|
| 2,216,617 | 10/1940 | Katz | ....................................... | 536/53 |
| 3,480,613 | 11/1969 | Walton | ............................... | 536/18.2 |
| 4,086,416 | 4/1978 | Acton et al. | ........................... | 536/24 |
| 4,447,600 | 5/1984 | Ogura et al. | ........................... | 536/23 |

Primary Examiner—Johnnie R. Brown

Attorney, Agent, or Firm—Oblon, Fisher, Spivak, McClelland & Maier

[57] ABSTRACT

This invention provides a novel compound having a formula such as

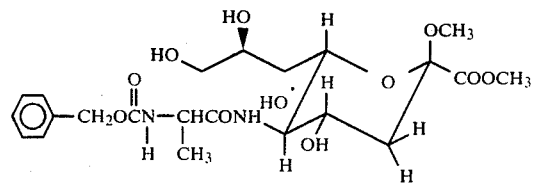

or

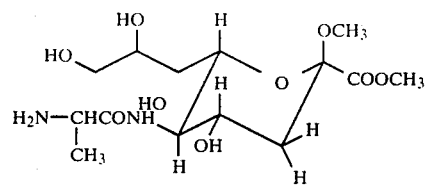

This invention also provides a process for preparing such a compound. The novel compound has an excellent immunological activity.

4 Claims, No Drawings

N-SUBSTITUTED NEURAMINIC ACID DERIVATIVES

BACKGROUND OF THE INVENTION

1. Field of the Invention

The present invention relates to novel N-substituted neuraminic acid derivatives having an excellent immunological activity and processes for preparation thereof.

2. Description of the Prior Art

So far, it has been known in the art that N-substituted neuraminic acids are present in many animals and on the cell surface of several bacterias as a complex of sialic acid such as glycoprotein, glycolipid, oligosaccharide or polysaccharide.

Recently, N-substituted neuraminic acids have become important substances in medicine and pharmaceutics relative to nerve function, cancer, inflammation, immunity, viral infection, differentiation, hormone receptor etc. However, the role of N-substituted neuraminic acids in the complex of sialic acid has not been ascertained yet.

Furthermore, N-substituted neuraminic acids have been studied by many organic chemists and therefore, many kinds of simple derivatives thereof have been obtained. But no derivative having an excellent immunological activity has been obtained yet.

On the other hand, the average span of human life has been extended because of improvements in medical treatment for malignant tumor of hematopoietic organ, many kinds of cancers, and collagen disease. On the other hand, with the great increase in use of medicines, for example, medicines for adrenal cortical hormone or immunosuppresant, a number of undesirable side effects arise together with lowering and decrease in immunological competence.

SUMMARY OF THE INVENTION

Under such circumstances, the inventors of the present invention have paid special attention to sialic acid which is a bio-inherent ingredient and they continued their research on control agents for immunity having few side effects because of its chemical modification and control effects for immunological surveillance. As a result of such research, the inventors have succeeded in finding the novel compounds of the present invention having immunoregulation effect in which suppressor T cell is activated and production of immunoglolulin of B cell is restrained.

The principal object of the present claimed invention is to provide novel compounds having an excellent immunological activity, especially the immunoregulation effect.

Another object of this invention is to provide effective processes for preparing the novel compounds.

These and other objects of this invention are made clear hereunder.

According to the present invention, novel N-substituted neuraminic acid derivatives having the following general formula (I) are provided.

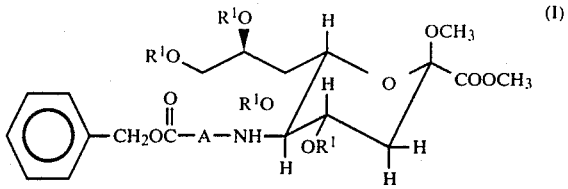

wherein $R^1$ is hydrogen or acetyl; and A is an amino acid residue having CO— and N— to which —NH and

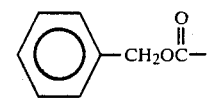

of the above formula bond respectively.

A in the formula (I) may preferably have the following formula;

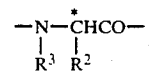

wherein $R^2$ is selected from

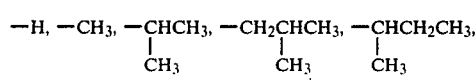

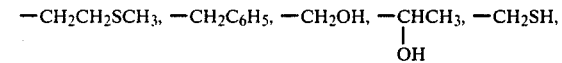

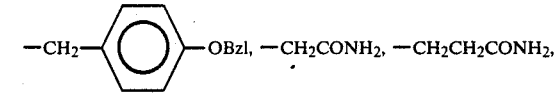

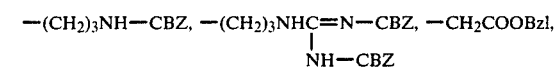

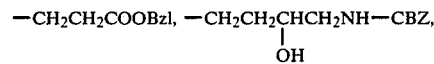

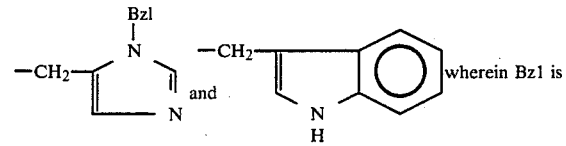

$-CH_2C_6H_5$ and CBZ is $C_6H_5CH_2OC-$; and $R^3$ is hydrogen or $R^2$ and $R^3$ form the ring selected from

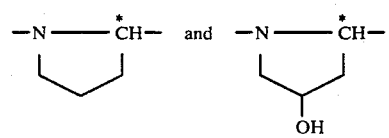

together with carbon atom and nitrogen atom to which R² and R³ bond. Relative to the steric configuration of asymmetric carbon atom indicated by an asterisk (*) such as

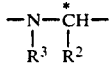

in the formula in the specification, the compounds having said asymmetric carbon atom may include D modification, L modification and racemic modification.

A compound of the present invention in which R¹ is hydrogen in the formula (I) identified above, may be prepared by a method such as the following reaction:

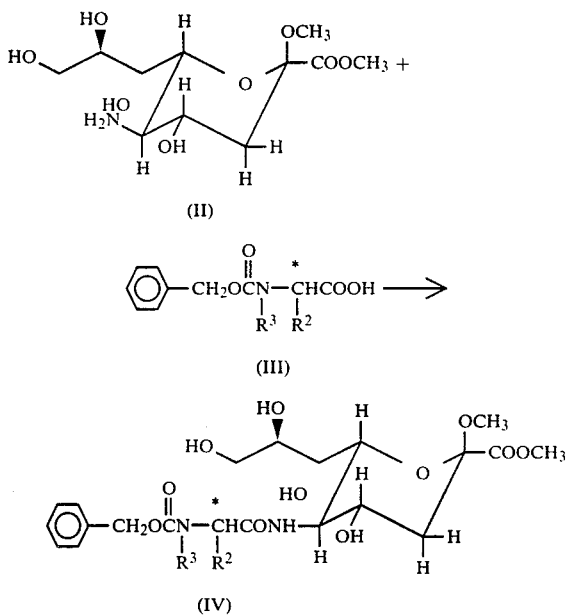

As a method for coupling reaction of said neuraminic acid having the formula (II) and N-benzyloxycarbonyl amino acid derivative having the formula (III), there are methods in which the compounds are previously made to activate the derivatives thereof and then the coupling reaction is carried out. That is, they are the methods of N terminal activation and C terminal activation (a method using acid chloride, a method using azide, a method using mixed acid anhydride, or a method using active ester).

As a concrete example of the activation, there is a method in which dicyclohexylcarbodiimide (hereunder referred to as DCC) is added to the mixture of compounds (II) and (III). Solvents such as methylene chloride, acetonitrile, dimethylformamide (hereunder referred to as DMF), pyridine or tetrahydrofuran may be employed as a solvent in the reaction using said DCC an anhydrous pyridine and DMF are preferably employed.

As for a general method for restraining the production of racemic modification in the coupling reaction, there is a method, known as the Eintopf method, in which DCC and N-hydroxy compound as a reagent for activating carboxyl group are added. Examples of N-hydroxy compound include N-hydroxysuccinic imide (hereunder referred to as HOSu), 1-hydroxybenzotriazole (hereunder referred to as HOBt), 3-hydroxy-4-oxo-3,4-dihydro-1,2,3-benzotriazine (hereunder referred to as HOOBt) and N-hydroxy-5-norbornene-2,3-dicarboximide (hereunder referred to as HONB). Tetrahydrofuran or dimethylformamide may be employed as a solvent for the reaction.

As a combination of said N-hydroxy compound and solvent, HONB and dimethylformamide may preferably be combined.

A compound of the present invention in which R¹ is acetyl in the formula (I) identified above, may be prepared by reacting said compound (IV) with acetic anhydride in anhydrous pyridine.

The method for preparing hydrochloride addition salt of compound (II) was described in J.A.C.S., 99, 8273 (1977).

Other novel N-substituted neuraminic acid derivatives are shown as the compounds having the formula (V):

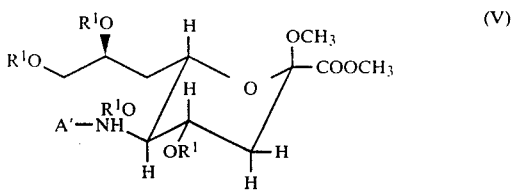

and inorganic and organic acid addition salts thereof, wherein R¹ is hydrogen or acetyl; and A' is an amino acid residue having CO— to which —NH of above formula bonds.

A' in the formula (V) may preferably have the following formula:

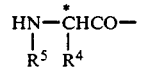

wherein R⁴ is selected from

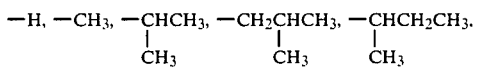

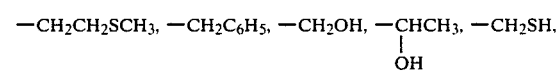

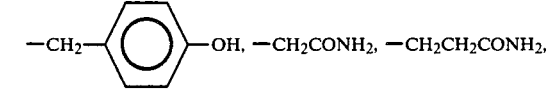

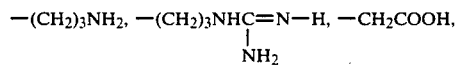

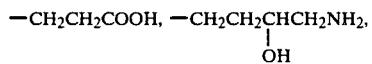

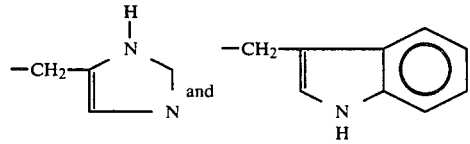

R⁵ is hydrogen or R⁴ and R⁵ form the ring selected from

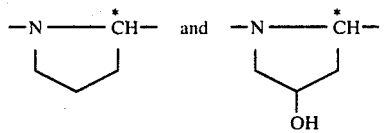

together with carbon atom and nitrogen atom to which R⁴ and R⁵ bond.

The compounds of the present invention having the formula (V) may be prepared by, for example, catalytic reduction of the compounds (I).

Said catalytic reduction may preferably be carried out by decomposition with hydrogenation in which Pd/c and methanol as a solvent are employed. Furthermore, compound (V) may easily be obtained as hydrochloride salts thereof by adding ammonium chloride to the reaction mixture.

According to the present invention, the compounds having the formula (I) and (V) have an excellent activity capable of adjusting the strength of the immune system. Activity capable of adjusting the strength of the immune system could be ascertained by the following method.

The function against the activation of mouse spleen lymphocyte by Con A:

As a T cell is non-specifically activated by Con A, one of the N-substituted neuraminic acid derivatives of the present invention was added to the reaction and then, the function thereof was studied. That is, Con A and a compound having the formula (I) or (V), for example, the compound prepared in Examples will be shown afterward, were respectively added to the spleen lymphocyte (SPC) which was taken from BALB/C mouse and the mixture was cultured for 20 hours or so on the micro plate with 5% $CO_2$ added to the mixture at 37° C. Thymidine labeled with tritium and SPC was collected further after culturing the mixture for 10 hours or so. The amount of $^3$H-thymidine taken in SPC was determined by using a scintillation counter.

Relative to a compound having the formula (I) and (IV), promotion and reinforcement on $^3$H-thymidine taken in was observed, and an improvement in the function against the activation of T-cell by Con A was also observed.

The function against the production of immunoglobulin of mouse spleen lymphocyte:

As for N-substituted neuraminic acid derivatives of the present invention which were indicated in the activation of T-cell in the previous experiment, the function against the production of immunoglobline was studied further by measuring the number of plaque-forming cells (PFC).

At first, red blood cells of sheep and one of the compounds having the formula (I) or (V), for example, the compound prepared in Examples will be shown afterward, was added to SPC and the mixture was cultured at 37° C. for 5 days. SRBC and complement were added again to the sensitized SPC thus obtained. The number of PFC was counted after said mixture was cultured in a Cunningham chamber at the temperature of 37° C. for between 3 and 12 hours.

Since decrease in the number of PFC was observed and the cell viability was the same as in the control, it was ascertained that repression against production of immunoglobulin was strengthened.

The compounds of the present invention showed an excellent activity in the two kinds of examination identified above. According to this fact, it was considered that the production of immunoglobulin was repressed by activating repressive T cell.

So far, lowering of the function of suppressor T cell has been observed in autoimmune diseases such as collagen disease. Accordingly, N-substituted neuraminic acid derivatives of the present invention having activation function to suppressor T cell are expected to be effective in clinical applications as an agent for adjusting the strength of the immune system.

The present invention will now be illustrated by referring to the following nonlimitative examples.

EXAMPLE 1

Preparation of methyl(methyl 5-(N-benzyloxycarbonylglycylamino)-3,5-dideoxy-β-D-glycero-D-galacto-2-nonulopyranosid)onate 3.0 g (0.01 mode) of methyl(methyl 5-amino-3,5-dideoxy- -D-glycero-D-galacto-2-nonulopyranosid)onate (compound (II)), 2.13 g (0.01 mole) of N-CBZ-glycine (compound (III)) and 3.1 g (0.015 mole) of DCC were dissolved in 350 ml of anhydrous pyridine and then, the mixture was stirred at room temperature for 48 hours. The resulting suspension was filtrated and the solvent was distilled off to dryness. Thereafter, it was subjected to silica gel column chromatography, and eluted with chloroform/methanol (5:1) and the 3.92 g of colorless amorphous substance was obtained (Yield: 80%).

Physical properties of the colorless amorphous substance

Decomposition point 190°–193° C.

Elemental analysis $C_{21}H_{30}N_2O_{11}\cdot(13/10)H_2O$; MW=509.89.

Calculation C: 49.47, H: 6.44, N: 5.49; Found C: 49.48, H: 6.63, N: 5.37.

---

IR $\nu_{max}^{KBr}$ cm$^{-1}$ 3,350 (—OH, —NH), 1,740 (—COOMe), $$1,700\ (-\mathrm{NHC-O-}),\ 1,655\ (-\mathrm{C-C-NH-})$$
$$\qquad\qquad\ \ \|\qquad\qquad\qquad\ \ \|\quad\|$$
$$\qquad\qquad\ \ O\qquad\qquad\qquad\ \ O$$

---

H-NMR$_{90\ MHz}^{ppm}$ (DMSO—d$_6$+D$_2$O, TMS); 1.58 (1H, dd, J=12.2 Hz, J=10.8 Hz, 3-Hax), 2.27 (1H, dd, J=12.2 Hz, J=4.5 Hz, 3-Heq), 3.19 (3H, S, 2—OMe), 3.77 (3H, S, —COOMe), 5.08 (2H, S,

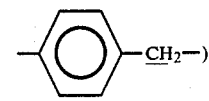

7.39 (5H, S, phenyl-H), [α]$_D^{20°}$ $^C$—29.6°; (C=1, MeOH).

EXAMPLE 2

Preparation of methyl (methyl 5-(N-benzyloxycarbonylglycylamino)-3,5-dideoxy- -D-glycero-D-galacto-2-nonulopyranosid)onate Example 2 was carried out by the same procedures as set forth in Example 1 except that 1.15 g (3.9 m mole) of compound (II), 0.82 g (3.9 m mole) of N-CBZ-glycine and 1.21 g (5.85 m mole) of DCC were dissolved in 35 ml of anhydrous DMF, and 1.32 g of product was obtained (Yield: 70%).

Physical properties of the product.

Decomposition point: 190°–193° C.

IR $\nu_{max}^{KBr}$ cm$^{-1}$ 3,350 (—OH, —NH), 1,740 (—COOMe),

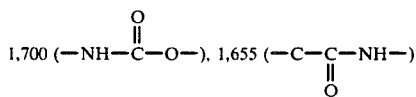

$^1$H-NMR$_{60}$ $_{MHz}$$^{ppm}$ (DMSO—d$_6$+CDCl$_3$+D$_2$O, TMS); 1.59 (1H, m, 3-Hax), 2.34 (1H, m, 3-Heq), 3.24 (3H, S, 2—OMe), 3.77 (3H, S, —COOMe), 5.08 (2H, S,

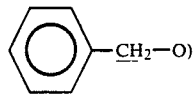

7.35 (5H, S, phenyl-H).

EXAMPLE 3

Preparation of methyl (methyl 5-(N-benzyloxycarbonylglycylamino)-3,5-dideoxy-β-D-glycero-D-galacto-2-nonulopyranosid)onate 1.0 (3.39 m mole) of compound (II) and 0.71 (3.39 m mole) of compound (III) were dissolved in 30 ml of DMF anhydride and then 0.31 ml of N-ethylmorpholine and 0.79 g (4.41 m mole) of HONB (N-hydroxy-5-norbornene-2,3-dicarboximide) were added thereto. Next, 0.91 g (4.41 m mole) of DCC was added thereto and then the mixture thus obtained was stirred for 48 hours at room temperature after a 3-hour stirring on cooling to a temperature of 0° C. The resulting suspension was filtrated and the solvent was distilled off to dryness. Thereafter, it was subjected to silica gel column chromatography, and eluted with chloroform/methanol (5:1) and then 1.35 g of colorless amorphous substance was obtained (Yield: 82%).

Physical properties of the substance
Decomposition point: 190°–193° C.
Elemental analysis C$_{21}$H$_{30}$N$_2$O$_{11}$, NW=486.47
Calculation C: 51.85, H: 6.22, N: 5.76, Found C: 51.80, H: 6.21, N: 5.64.

IR $\nu_{max}^{KBr}$ cm$^{-1}$ 3,350 (—OH, —NH), 1,740 (—COOMe),

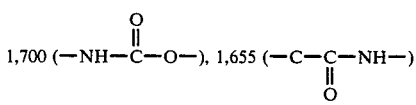

$^1$H-NMR$_{90}$ $_{MHz}$$^{ppm}$ (DMSO—d$_6$, TMS); 1.52 (1H, dd, J=12.2 Hz, J=10.8 Hz, 3-Hax), 2.19 (1H, dd, J=12.2 Hz, J=4.5 Hz, 3-Heq), 3.18 (3H, S, 2—OMe), 3.71 (3H, S, —COOMe), 5.04 (2H, S,

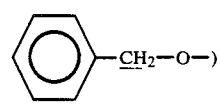

7.35 (5H, S, phenyl-H).

EXAMPLE 4

Preparation of methyl(methyl 5-(N-benzyloxycarbonyl-L-alanylamino)-3,5-dideoxy-β-D-glycero-D-galacto-2-nonulopyranosid)onate Example 4 was carried out by the same procedures as set forth in Example 1 except that 1.0 g (3.39 m mole) of compound II, 0.76 g (3.9 m mole) of N-CBZ-L-alanine and 0.84 g of DCC were dissolved in 100 ml of anhydrous pyridine and therefore, 1.18 g of colorless amorphous substance was obtained (Yield: 70%).

Physical properties of the substance
Melting point: 74°–77° C.; Decomposition point: 193°–195° C.
Elemental analysis C$_{22}$H$_{32}$N$_2$O$_{11}$, MW=500.51
Calculation C: 52.79, H: 6.44, N: 5.60; Found value C: 52.77, H: 6.42, N: 5.58.

IR $\nu_{max}^{KBr}$ cm$^{-1}$ 3,350 (—OH, —NH), 1,740 (—COOMe),

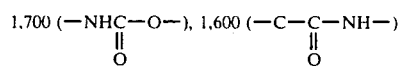

$^1$H-NMR$_{90}$ $_{MHz}$$^{ppm}$ (DMSO—d$_6$+CDCl$_3$+D$_2$O, TMS); 1.40 (3H, d, J=7.07 Hz >CH—CH$_3$), 1.68 (1H, dd, J=13.5 Hz, J=10.8 Hz, 3-Hax), 2.38 (1H, dd, J=13.5 Hz, J=4.9 Hz, 3-Heq), 3.26 (3H, S, 2—OCH$_3$), 3.73 (3H, S, —COOCH$_3$), 5.05 (2H, S,

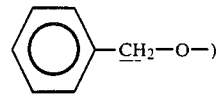

7.29 (5H, S, phenyl-H), [α]$_D^{20° C.}$ −29.9°(C=1, MeOH).

EXAMPLE 5

Preparation of methyl(methyl 5-(N-benzyloxycarbonyl-L-alanylamino)-3,5-dideoxy-β-D-glycero-D-galacto-2-nonulopyranosid)onate Example 5 was carried out by the same procedures as set forth in Example 3 except that 0.76 g (3.39 m mole) of N-CBZ-L-alanine was used instead of N-CBZ-glycine and therefore, 1.40 g of product was obtained (Yield: 83%).

Physical properties of the product
Decomposition point 198°–201° C.

EXAMPLE 6

Preparation of methyl(methyl 5-(N-benzyloxyycarbonyl-L-leucylamino)-3,5-dideoxy-β-D-glycero-D-galacto-2-nonulopyranosid)onate Example 6 was carried out by the same procedures as set forth in Example 4 except that 0.9 g (3.39 m mole) of N-CBZ-L-leucine was used instead of N-CBZ-L-alanine and solvent of chloroform/methanol (10:1) was used in elution and therefore, 1.38 g of product was obtained (Yield: 75%).

Physical properties of the product
Melting point: 76°–81° C., Decomposition point: 156°–158° C.
Elemental analysis C$_{25}$H$_{38}$N$_2$O$_{11}$.(1/5)H$_2$O, MW=546.20
Calculation C: 54.98, H: 7.09, N: 5.13; Found value C: 54.97, H: 6.95, N: 5.05.

IR $\nu_{max}^{KBr}$ cm$^{-1}$ 3,375 (—OH, —NH—), 1,740 (—COOMe),

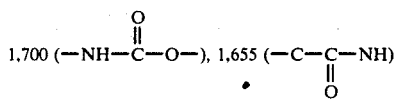

1,700 (—NH—C—O—), 1,655 (—C—C—NH)

$^1$H-NMR$_{90}$ $_{MHz}$$^{ppm}$ (DMSO—d$_6$+CDCl$_3$+D$_2$O, TMS); 0.94 (6H, d, J=4.9 Hz,

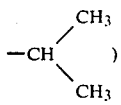

2.37 (1H, dd, J=13.5 Hz, J=5.4 Hz, 3-Heq), 3.27 (3H, S, 2—OMe), 3.78 (3H, S, —COOC$_3$), 5.09 (2H, S,

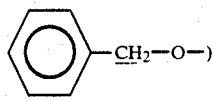

7.34 (5H, S, phenyl-H), [α]$_D^{20°}$ $^{C.}$—29.3° (C=1, MeOH).

As another method, the same compound as set forth in Example 6 was prepared by the same procedures as set forth in Example 5 except that 5.39 g of N-CBZ-L-leucine was used instead of N-CBZ-L-alanine, and 6.0 g of the compound II, 1.86 ml of N-ethylmorpholine and 4.74 g of HONB were used. Therefore, 7.7 g of product was obtained (Yield 70%) and the physical properties of the product were the same as shown above.

EXAMPLE 7

Preparation of methyl(methyl 5-N-(benzyloxycarbonyl-L-phenylalanylamino)-3,5-dideoxy-β-D-glycero-D-galacto-2-nonulopyranosid)onate Example 7 was carried out by the same procedures as set forth in Example 4 except that 1.015 g (3.39 m mole) of N-CBZ-L-phenylalanine was used instead of N-CBZ-L-alanine and therefore, 1.52 g of product was obtained (Yield: 78%).

Physical properties of the product

Melting point: 75°-80° C. Decomposition point: 168°-170° C.

Elemental analysis C$_{28}$H$_{36}$N$_2$O$_{11}$, MW=576.60

Calculation C: 58.33, H: 6.29, N: 4.86; Found C: 58.32, H: 6.17, N: 4.83.

IR $\nu_{max}^{KBr}$ cm$^{-1}$ 3,375 (—OH, —NH—), 1,735 (—COOMe), 1,700 (—NH—C—O—), 1,655 (—C—C—NH—)

$^1$H-NMR$_{90}$ $_{MHz}$$^{ppm}$ (DMSO—d$_6$+D$_2$O, TMS); 1.55 (1H, dd, J=12.6 Hz, J=10.8 Hz, 3-Hax), 2.22 (1H, dd, J=12.6 Hz, J=4.05 Hz, 3-Heq), 3.21 (3H, S, 2—OCH$_3$), 3.74 (3H, S, —COOCH$_3$), 4.96 (2H, S,

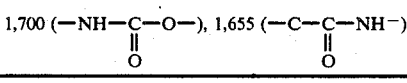

[α]$_D^{20°}$ $^{C.}$—22.8° (C=1, MeOH).

As another method, the same compound as set forth in Example 7 was prepared by the same procedures as set forth in Example 5 except that 6.08 of N-CBZ-L-phenylalanine was used instead of N-CBZ-L-alanine, and 6.0 g of the compound II, 1.86 ml of N-ethylmorpholine and 4.74 g of HONB were used. Therefore, 8.4 g of product was obtained (Yield 72%) and the physical properties of the product were the same as shown above.

EXAMPLE 8

Preparation of methyl(methyl 5-(N-benzyloxycarbonyl-serylamino)-3,5-dideoxy-β-D-glycero-D-galacto-2-nonulopyranosid)onate Example 8 was carried out by the same procedures as set forth in Example 4 except that 0.81 g (3.39 m mole) of N-CBZ-L-serine was used instead of N-CBZ-L-alanine and therefore, 1.33 g of product was obtained (Yield: 76%).

Physical properties of the product

Melting point: 71°-76° C., Decomposition point: 147°-151° C.

Elemental analysis C$_{22}$H$_{32}$N$_2$O$_{12}$, MW=516.51

Calculation C: 51.16, H: 6.24, N: 5.42; Found C: 51.13, H: 6.17, N: 5.46.

IR $\nu_{max}^{KBr}$ cm$^{-1}$ 3,375 (—OH, —NH), 1,740 (—COOMe), 1,700 (—NH—C—O—), 1,655 (—C—C—NH—)

$^1$H-NMR$_{90}$ $_{MHz}$$^{ppm}$ (DMSO—d$_6$+D$_2$O, TMS); 1.51 (1H, dd, J=12.6 Hz, J=11.25 Hz, 3-Hax), 2.21 (1H, dd, J=12.6 Hz, J=5.0 Hz, 3-Heq), 3.17 (3H, S, 2—OCH$_3$), 3.72 (3H, S, —COOCH$_3$), 5.04 (2H, S,

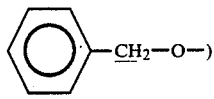

7.37 (5H, S, phenyl-H), [α]$_D^{20°}$ $^{C.}$—22.63° (C=1, MeOH).

As another method, the same compound as set forth in Example 8 was prepared by the same procedures as set forth in Example 5 except that 4.86 g of N-CBZ-L-serine was used instead of N-CBZ-L-alanine, and 6.0 g of the compound II, 2.41 ml of N-ethylmorpholine and 4.73 g of HONB were used. Therefore, 7.4 g of product was obtained (Yield 70%) and the physical properties of the product were the same as shown above.

EXAMPLE 9

Preparation of methyl (methyl 5-(N-benzyloxycarbonyl-L-valylamino)-3,5-dideoxy-β-D-glycero-D-galacto-2-nonulopyranosid)onate Example 9 was carried out by the same procedures as set forth in Example 4 except that 0.85 g (3.39 m mole)

of N-CBZ-L-valine was used in instead of N-CBZ-L-alanine and solvent of chloroform/methanol (10:1) was used in elution and therefore, 1.43 g of products was obtained (Yield: 80%).

Physical properties of the product

Melting point: 78°–83° C., Decomposition point: 153°–154° C. Elemental analysis $C_{24}H_{36}N_2O_{11} \cdot (2/5)$-$H_2O$, MW=535.77

Calculation C: 53.80, H: 6.92, N: 5.23; Found C: 53.83, H: 6.81, N: 5.18.

---

IR $\nu_{max}^{KBr}$ cm$^{-1}$ 3,375 (—OH, —NH), 1,730 (—COOCH$_3$),

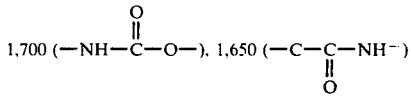

1,700 (—NH—C—O—), 1,650 (—C—C—NH—)

---

$^1$H-NMR$_{90}$ $_{MHz}$$^{ppm}$ (DMSO—d$_6$+D$_2$O, TMS); 0.87; 0.90 (6H, d, J=6.6 Hz,

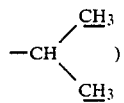

1.55 (1H, dd, J=12.7 Hz, J=10.9 Hz, 3-Hax), 1.73–2.10 (1H, m,

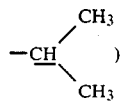

2.23 (1H, dd, J=12.7 Hz, J=4.4 Hz, 3-Heq), 3.19 (3H, S, 2—OCH$_3$), 3.74 (3H, S, —COOCH$_3$), 3.19–3.91 (8H, m, sialy-H,

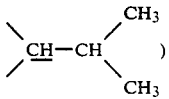

5.05 (2H, S, C$_6$H$_5$CH$_2$O—), 7.37 (5H, S, C$_6$H$_5$—), $[\alpha]_D^{20\,°\,C.}$ —26.2° (C=1, MeOH).

As another method, the same compound as set forth in Example 9 was prepared by the same procedures as set forth in Example 5 except that 5.62 g of N-CBZ-L-valine was used instead of N-CBZ-L-alanine, and 6.0 g of the compound II, 2.35 ml of N-ethylmorpholine and 4.73 g of HONB were used. Therefore, 7.84 g of product was obtained (Yield 73%) and the physical properties of the product were the same as shown above.

EXAMPLE 10

Preparation of methyl (methyl 5-(N-benzyloxycarbonyl-L-methionylamino)-3,5-dideoxy-β-D-glycero-D-galacto-2-nonulopyranosid)onate Example 10 was carried out by the same procedures as set forth in Example 4 except that 0.96 g (3.39 m mole) of N-CBZ-L-methionine was used instead of N-CBZ-L-alanine and solvent of chloroform/methanol (10:1) was used in elution and therefore, 1.48 g of product was obtained (Yield 78%).

Physical properties of the product

Melting point: 67°–72° C., Decomposition: 170°–177° C.

Elemental analysis $C_{24}H_{36}N_2O_{11}S$ MW=560.63

Calculation C: 51.42, H: 6.47, N: 5.00; Found C: 51.28, H: 6.37, N: 4.97.

---

IR $\nu_{max}^{KBr}$ cm$^{-1}$ 3,350 (—OH, —NH), 1,730 (—COOCH$_3$), 1,700 (—NH—C—O—), 1,650 (—C—C—NH—)

---

$^1$H-NMR$_{90}$ $_{MHz}$$^{ppm}$ (DMSO—d$_6$+D$_2$O, TMS); 1.56 (1H, dd, J=12.7 Hz, J=11.0 Hz, 3-Hax), 1.71–2.00 (2H, m, CH$_3$SCH$_2$CH$_2$—), 2.04 (3H, S, CH$_3$—S—), 2.25 (1H, dd, J=12.7 Hz, J=4.0 Hz, 3-Heq), 2.35–2.62 (2H, m, CH$_3$SCH$_2$CH$_2$—), 3.19 (3H, S, 2—OCH$_3$), 3.75 (3H, S, —COOCH$_3$), 3.19–3.85 (8H, m, sialyl-H, CH$_3$SCH$_2$CH$_2$CH<), 5.05 (2H, S, C$_6$H$_5$CH$_2$O—), 7.37 (5H, S, C$_6$H$_5$—), $[\alpha]_D^{20\,°\,C.}$ —27.5° (C=1, MeOH).

As another method, the same compound as set forth in Example 10 was prepared by the same procedures as set forth in Example 5 except that 5.76 g of N-CBZ-L-methionine was used instead of N-CBZ-L-alanine, and 6.0 g of the compound II, 2.35 ml of N-ethylmorpholine and 4.73 g of HONB were used. Therefore, 8.1 g of product was obtained (Yield 71%) and the physical properties of the product were the same as shown above.

EXAMPLE 11

Preparation of methyl (methyl 5-(glycylamino)-3,5-dideoxy-β-D-glycero-D-galacto-2-nonulopyranosid)onate 300 mg (1.34 m mole) of methyl (methyl 5-(N-benzyloxycarbonylglycylamino)-3,5-dideoxy-β-D-glycero-D-galacto-2-nonulopyranoside)onate was dissolved into anhydrous methanol and thereafter, 301 mg (0.62 m mole) of Pd/c (10%) was added thereto. Then, the mixture was stirred under hydrogen gas at room temperature for 16 hours. The resulting reaction suspension was filtrated and the solvent was distilled off to dryness, 210 mg of colorless amorphous substance was obtained (Yield 97%).

Physical properties of the substance

Decomposition point: 126°–130° C.

IR $\nu_{max}^{KBr}$ cm$^{-1}$ 1,740 (—COOCH$_3$)

$^1$H-NMR$_{60}$ $_{MHz}$$^{ppm}$ (CD$_3$OD, TMS); 1.61 (1H, m, 3-Hax), 2.40 (1H, m, 3-Heq), 3.27 (3H, S, 2—OCH$_3$), 3.81 (3H, S, —COOCH$_3$), 3.41–4.36 (9H, m, sialyl-H, NH$_2$CH$_2$CO—).

EXAMPLE 12

Preparation of hydrochloride addition salt of methyl (methyl 5-(glycylamino)-3,5-dideoxy-α-D-glycero-D-galacto-2-nonulopyranosid)onate 500 mg (10.28 m mole) of methyl (methyl 5-(N-benzyloxycarbonylglycylamino)-3,5-deoxy-β-D-glycero-D-galacto-2-nonulopyranosid)onate was dissolved into anhydrous methanol and thereafter, 428 mg (0.4 m mole) of Pd/C (10%) and 200 mg (3.67 m mole) of NH$_4$Cl were added thereto. Then, the mixture was stirred under hydrogen gas at room temperature for 20 hours. The resulting reaction suspension was filtrated and the solvent was distilled off to dryness, 380 mg of colorless amorphous substance was obtained (Yield 95%).

Physical properties of the substance

Decomposition point: 145°–150° C.

IR $V_{max}^{KBr}$ cm$^{-1}$ 1,740 (—COOCH$_3$), $^1$H-NMR$_{60}$ $_{MHz}^{ppm}$ (CD$_3$OD, TMS); 1,62 (1H, m, 3-Hax), 2.36 (1H, m, 3-Heq), 3.27 (3H, S, 2—OCH$_3$), 3.83 (3H, S, —COOCH$_3$), 3.40–4.20 (9H, m, sialyl-H, NH$_2$CH$_2$CO—).

EXAMPLE 13

Preparation of methyl methyl 5-(N-benzyloxycarbonyl-glycylamino)-3,5-dideoxy-4,7,8,9-tetra-O-acetyl-β-D-glycero-D-galacto-2-nonulopyranosid)onate 0.15 g (0.31 m mole) of methyl (methyl 5-(N-benzyloxycarbonylglycylamino)-3,5-dideoxy-β-D-glycero-D-galacto-2-nonulopyranosid)onate was dissolved into 3 ml of anhydrous pyridine and thereafter, 3 ml of acetic anhydride was added thereto. Then, the mixture was stirred at room temperature for two hours. The resulting reaction mixture was filtrated and the solvent was distilled off to dryness. Thereafter, it was subjected to silica gel chloramography, and eluted with chloroform-/methanol (30:1), 0.17 g of colorless amorphous substance was obtained (Yield 85%).

Physical properties of the substance

Melting point: 70°–74° C., Decomposition point: 130°–160° C.

IR $v_{max}^{KBr}$ cm$^{-1}$ 3,370 (—NH), 1,740 (—COOCH$_3$), $^1$H-NMR$_{90}$ $_{MHz}^{ppm}$ (CDCl$_3$, TMS); 1.57–2.14 (13H, m, CH$_3$CO—, 3-Hax), 2.47 (1H, dd, J=13.0 Hz, J=5.27 Hz, 3-Heq), 3.23 (3H, S, 2—OCH$_3$), 3.80 (3H, S, —COOCH$_3$), 5.14 (2H, S,

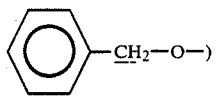

3.61–5.50 (9H, m, —NHCH$_2$—CO—, Sialyl-H), 5.62.6.62 (2H, broad S, —NH—), 7.35 (5H, S, phenyl-H).

EXAMPLE 14

Preparation of methyl (methyl 5-(N-benzyloxycarbonyl-D-alanylamino)-3,5-dideoxy-β-D-glycero-D-galacto-2-nonulopyranosid)onate Example 14 was carried out by the same procedures as set forth in Example 5 except that 0.76 g of N-CBZ-D-alanine was used instead of N-CBZ-L-alanine, and 1.0 g of compound (II), 0.36 ml of N-ethylmorpholine and 0.79 g of HONB were used. Therefore, 1.2 g product was obtained (Yield 70%).

Physical properties of the product

Decomposition 209°–213° C.

Elemental analysis C$_{12}$H$_{32}$N$_2$O$_{11}$, MW=500.51

Calculation C: 52.79, H: 6.44, N: 5.60; Found C: 52.97, H: 6.40, N: 5.73.

IR $V_{max}^{KBr}$ cm$^{-1}$ 3,400 (—OH,—NH), 1,740 (—COOCH$_3$),

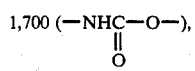

$^1$H-NMR$_{90}$ $_{MHz}^{ppm}$ (DMSO—d$_6$+D$_2$O, TMS); 1.26 (3H, d, J=7.07 Hz, >CH—CH$_3$), 1.52 (1H, dd, J=13.0 Hz, J=10.8 Hz, 3-Hax), 2.21 (1H, dd, J=13.0 Hz, J=4.5 Hz, 3-Heq), 3.18 (3H, S, 2—OCH$_3$), 3.74 (3H, S, —COOCH$_3$), 5.04 (2H, S, φ—CH$_2$—O—), 7.37 (5H, S, phenyl-H), [α]$_D^{22.5°}$ $^C$ −12.91° (C=1, MeOH).

EXAMPLE 15

Preparation of methyl (methyl 5-(N-benzyloxycarbonyl-DL-alanylamino)-3,5-dideoxy-β-D-glycero-D-galacto-2-nonulopyranosid)onate Example 15 was carried out by the same procedures as set forth in Example 5 except that 0.76 g of N-CBZ-DL-alanine was used instead of N-CBZ-L-alanine, and 1.0 g of compound (II), 0.36 ml of N-ethylmorpholine and 0.79 g of HONB were used. Therefore, 1.25 g of product was obtained (Yield 74%).

Physical properties of the product

Decomposition point 192°–195° C.

Elemental analysis C$_{12}$H$_{32}$N$_2$O$_{11}$, MW=500.51,

Calculation C: 52.79, H: 6.44, N: 5.60; Found C: 52.88, H: 6.30, N: 5.65.

$^1$H-NMR$_{400}$ $_{MHz}^{ppm}$ (DMSO—d$_6$+D$_2$O, TMS), 1.218; 1.223 (6H, d, J=7.10 Hz, >CH—CH$_3$), 1.503 (1H, m, 3-Hax), 2.161 (1H, m, 3-Heq), 3.168; 3.176 (3H, S, 2—OCH$_3$), 4.045; 4.142 (1H, m, >CH—CH$_3$).

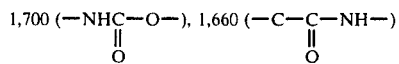

EXAMPLE 16

Preparation of methyl (methyl 5-(N-benzyloxycarbonyl-D-valylamino)-3,5-dideoxy-β-D-glycero-D-galacto-2-nonulopyranosid)onate Example 16 was carried out by the same procedures as set forth in Example 5 except that 0.43 g of N-CBZ-D-valine was used instead of N-CBZ-L-alanine, and 0.5 g of compound II, 0.18 ml of N-ethylmorpholine and 0.40 g of HONB were used. Therefore, 627 mg of product was obtained (Yield 70%).

Physical properties of the product

Decomposition point 229°–231° C.

Elemental analysis C$_{24}$H$_{36}$N$_2$O$_{11}$, MW=528.56

Calculation C: 54.54, H: 6.87, N: 5.30; Found C: 54.61, H: 6.72, N: 5.44.

IR $v_{max}^{KBr}$ cm$^{-1}$ 3,400 (—OH, —NH), 1,740 (—COOCH$_3$),

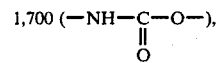

[α]$_D^{25.6°}$ $^{C.}$ −33.8° (C=1, DMF).

EXAMPLE 17

Preparation of methyl (methyl 5-L-alanylamino-3,5-dideoxy-β-D-glycero-D-galacto-2-nonulopyranosid)onate Example 17 was carried out by the same procedures as set forth in Example 11 except that 1.5 g of the colorless amorphous substance prepared in Example 4 was used as a starting material. Therefore, 0.77 g of product was obtained (Yield 70%).

Physical properties of the product obtained

Decomposition point 164°–170° C.

IR $v_{max}^{KBr}$ cm$^{-1}$ 3,300 (—NH$_2$, —OH), 1,740 (—COOCH$_3$)

$^1$H-NMR$_{90\ MHz}$$^{ppm}$ (DMSO—d$_6$+D$_2$O, TMS), 1.19 (3H, d, J=6.8 Hz, —CH$_3$), 3.17 (3H, S, 2—OCH$_3$), 3.73 (3H, S, —COOCH$_3$).

EXAMPLE 18

Preparation of methyl (methyl 5-L-leucylamino-3,5-dideoxy-β-D-glycero-D-galacto-2-nonulopyranosid)onate Example 18 was carried out by the same procedures as set forth in Example 11 except that 1.5 g of product prepared in Example 6 was used as a starting material. Therefore, 0.93 g of product was obtained (Yield 82%).

Physical properties of the product obtained
Decomposition point 196°–199° C.
IR $\nu_{max}^{KBr}$ cm$^{-1}$ 3,400–3,200 (—NH$_2$, —OH), 1,740 (—COOCH$_3$)
$^1$H-NMR$_{90\ MHz}$$^{ppm}$ (DMSO—d$_6$, TMS), 0.89 (6H, d, J=6.18 Hz,

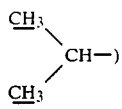

3.18 (3H, S, 2—OCH$_3$), 3.71 (3H, S, —COOCH$_3$).

EXAMPLE 19

Preparation of methyl (methyl 5-L-phenyl-alanylamino-3,5-dideoxy-β-D-glycero-D-galacto-2-nonulopyranosid)onate Example 19 was carried out by the same procedures as set forth in Example 11 except that 1.5 g of the product prepared according to Example 7 was used as a starting material. Therefore, 0.91 g of product was obtained (Yield 79%).

Physical properties of the product obtained
Decomposition point 181°–187° C.
IR $\nu_{max}^{KBr}$ cm$^{-1}$ 3,350 (—OH, —NH$_2$), 1,7400 (—COOCH$_3$)
$^1$H-NMR$_{90\ MHz}$$^{ppm}$ (DMSO—d$_6$, TMS), 3.18 (3H, S, 2—OCH$_3$), 3.71 (3H, S, —COOCH$_3$).

EXAMPLE 20

Preparation of methyl (methyl 5-L-serylamino 3,5-dideoxy-β-D-glycero-D-galacto-2-nonulopyranosid)onate Example 20 was carried out by the same procedures as set forth in Example 11 except that 1.5 g of the product prepared in Example 8 was used as a starting material. Therefore, 0.91 g of product was obtained (Yield 82%).

Physical properties of the product obtained
Decomposition point 118°–124° C.
IR $\nu_{max}^{KBr}$ cm$^{-1}$ 3,350 (—OH, —NH$_2$), 1,740 (—COOCH$_3$)
$^1$H-NMR$_{90\ MHz}$$^{ppm}$ (DMSO—d$_6$+D$_2$O, TMS), 3.17 (3H, S, 2—OCH$_3$), 3.73 (3H, S, —COOCH$_3$),

EXAMPLE 21

Preparation of methyl (methyl 5-L-varylamino-3,5-dideoxy-β-D-glycero-D-galacto-2-nonulopyranosid)onate Example 21 was carried out by the same procedures as set forth in Example 11 except that 1.5 g of the product prepared in Example 9 was used as a starting material.

Therefore, 0.93 g of product was obtained (Yield 83%).

Physical properties of the product obtained
Decomposition point 112°–118° C.
IR $\nu_{max}^{KBr}$ cm$^{-1}$ 3,300–3,400 (—OH, —NH$_2$), 1,740 (—COOCH$_3$).
$^1$H-NMR$_{90\ MHz}$$^{ppm}$ (DMSO—d$_6$, TMS) 0.897 (6H, d, J=6.2 Hz,

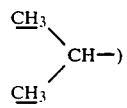

3.180 (3H, S, 2—OCH$_3$), 3.710 (3H, S, —COOCH$_3$).

What is claimed is:

1. An N-substituted neuraminic acid compound of the formula:

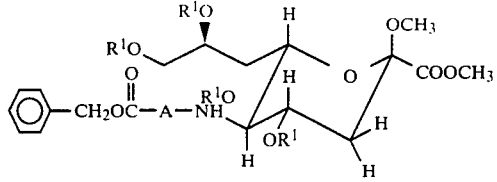

wherein R$^1$ is hydrogen or acetyl; and A is an amino acid residue having CO— and N-radicals to which —NH and

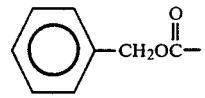

of the above formula bond respectively.

2. A compound as set forth in claim 1 wherein A in the formula has the following formula:

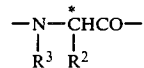

wherein
R$^2$ is selected from the group consisting of

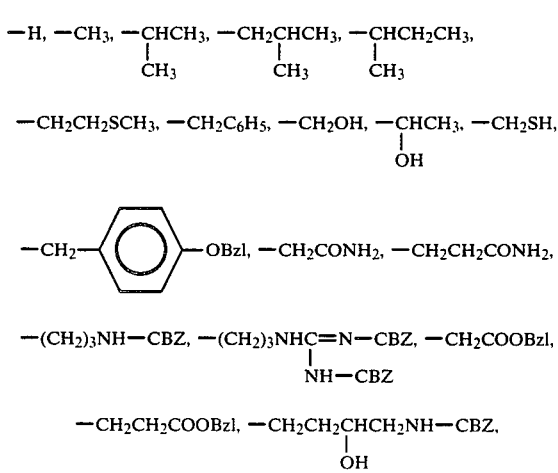

-continued

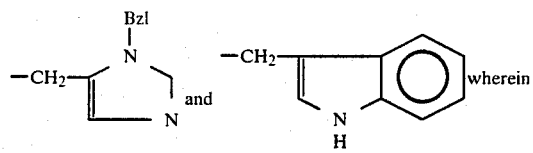

BZl is CH$_2$C$_6$H$_5$ and CBZ is C$_6$H$_5$CH$_2$O$\overset{O}{\overset{\|}{C}}$—; and R$^3$ is hydrogen or R$^2$ and R$^3$ form the ring selected from

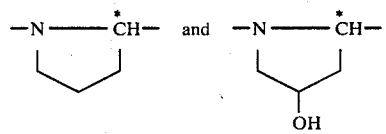

together with carbon atom and nitrogen atom to which R$^2$ and R$^3$ bond.

3. An N-substituted neuraminic acid compound of of the formula:

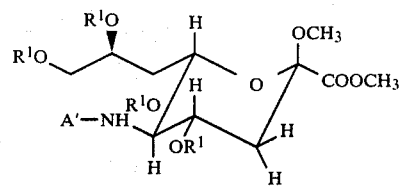

wherein R$^1$ is hydrogen or acetyl; and A' is an amino acid residue having a CO-radical to which —NH of the above formula bonds.

4. A compound as set forth in claim 3 wherein A' in the formula has the following formula:

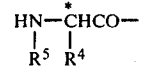

wherein R$^4$ is selected from the group consisting of

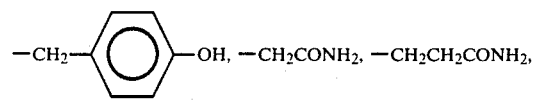

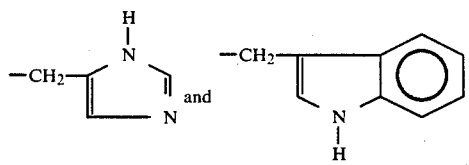

wherein BZ1 is —CH$_2$C$_6$H$_5$ and CBZ is C$_6$H$_5$CH$_2$OC—; and

R$^5$ is hydrogen or R$^4$ and R$^5$ form the ring selected from

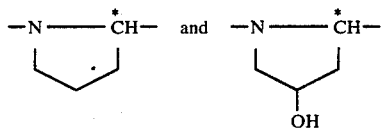

together with carbon atom and nitrogen atom to which R$^4$ and R$^5$ bond.

* * * * *